US009833347B2

(12) United States Patent
Christakis et al.

(10) Patent No.: US 9,833,347 B2
(45) Date of Patent: Dec. 5, 2017

(54) APPARATUSES FOR MANIPULATING MEDICAL DEVICES AND RELATED METHODS FOR USE

(71) Applicant: Boston Scientific Scimed, Inc., Maple Grove, MN (US)

(72) Inventors: Laura Elizabeth Christakis, Worcester, MA (US); Colby Harris, Weston, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 134 days.

(21) Appl. No.: 14/667,370

(22) Filed: Mar. 24, 2015

(65) Prior Publication Data

US 2015/0272760 A1 Oct. 1, 2015

Related U.S. Application Data

(60) Provisional application No. 61/970,180, filed on Mar. 25, 2014.

(51) Int. Cl.
*A61F 2/966* (2013.01)
*A61F 2/95* (2013.01)
*A61F 2/04* (2013.01)
*A61B 17/00* (2006.01)
*A61F 2/958* (2013.01)

(52) U.S. Cl.
CPC ............... *A61F 2/966* (2013.01); *A61F 2/95* (2013.01); *A61B 2017/0034* (2013.01); *A61B 2017/00296* (2013.01); *A61F 2/958* (2013.01); *A61F 2002/044* (2013.01); *A61F 2002/9528* (2013.01); *A61F 2002/9534* (2013.01); *A61F 2002/9665* (2013.01)

(58) Field of Classification Search
CPC ................ A61F 2002/9528; A61F 2002/9534
See application file for complete search history.

(56) References Cited

U.S. PATENT DOCUMENTS

| 5,643,309 | A | * | 7/1997 | Myler | ............... A61F 2/91 606/191 |
| 5,911,725 | A | * | 6/1999 | Boury | ............... A61B 17/22 606/108 |
| 6,676,692 | B2 | | 1/2004 | Rabkin et al. | |
| 6,821,291 | B2 | | 11/2004 | Bolea et al. | |
| 8,187,284 | B2 | | 5/2012 | Jordan et al. | |
| 2002/0161377 | A1 | * | 10/2002 | Rabkin | ............... A61F 2/95 606/108 |

(Continued)

FOREIGN PATENT DOCUMENTS

EP 2252240 B1 8/2012

*Primary Examiner* — Shaun L David
(74) *Attorney, Agent, or Firm* — Seager, Tufte & Wickem, LLP

(57) ABSTRACT

Apparatuses for manipulating a collapsible medical device include a sheath, a first shaft including a first grasping member and a second grasping member. The second grasping member is separated from the first grasping member by a distance. The collapsible medical device may be manipulated by actuating the first grasping member and the second grasping member and by increasing the distance between the first grasping member and the second grasping member. Methods of using the apparatuses are provided.

16 Claims, 9 Drawing Sheets

(56) References Cited

U.S. PATENT DOCUMENTS

| | | | |
|---|---|---|---|
| 2006/0030865 A1* | 2/2006 | Balg | A61F 2/95 |
| | | | 606/113 |
| 2006/0190075 A1 | 8/2006 | Jordan et al. | |
| 2007/0027520 A1* | 2/2007 | Sherburne | A61F 2/958 |
| | | | 623/1.11 |
| 2010/0331949 A1* | 12/2010 | Habib | A61B 18/1477 |
| | | | 623/1.11 |
| 2011/0071613 A1 | 3/2011 | Wood et al. | |
| 2012/0010699 A1* | 1/2012 | Vesely | A61F 2/2418 |
| | | | 623/2.11 |
| 2012/0310327 A1 | 12/2012 | McHugo | |
| 2013/0060323 A1 | 3/2013 | McHugo | |
| 2013/0090714 A1 | 4/2013 | McHugo | |

* cited by examiner

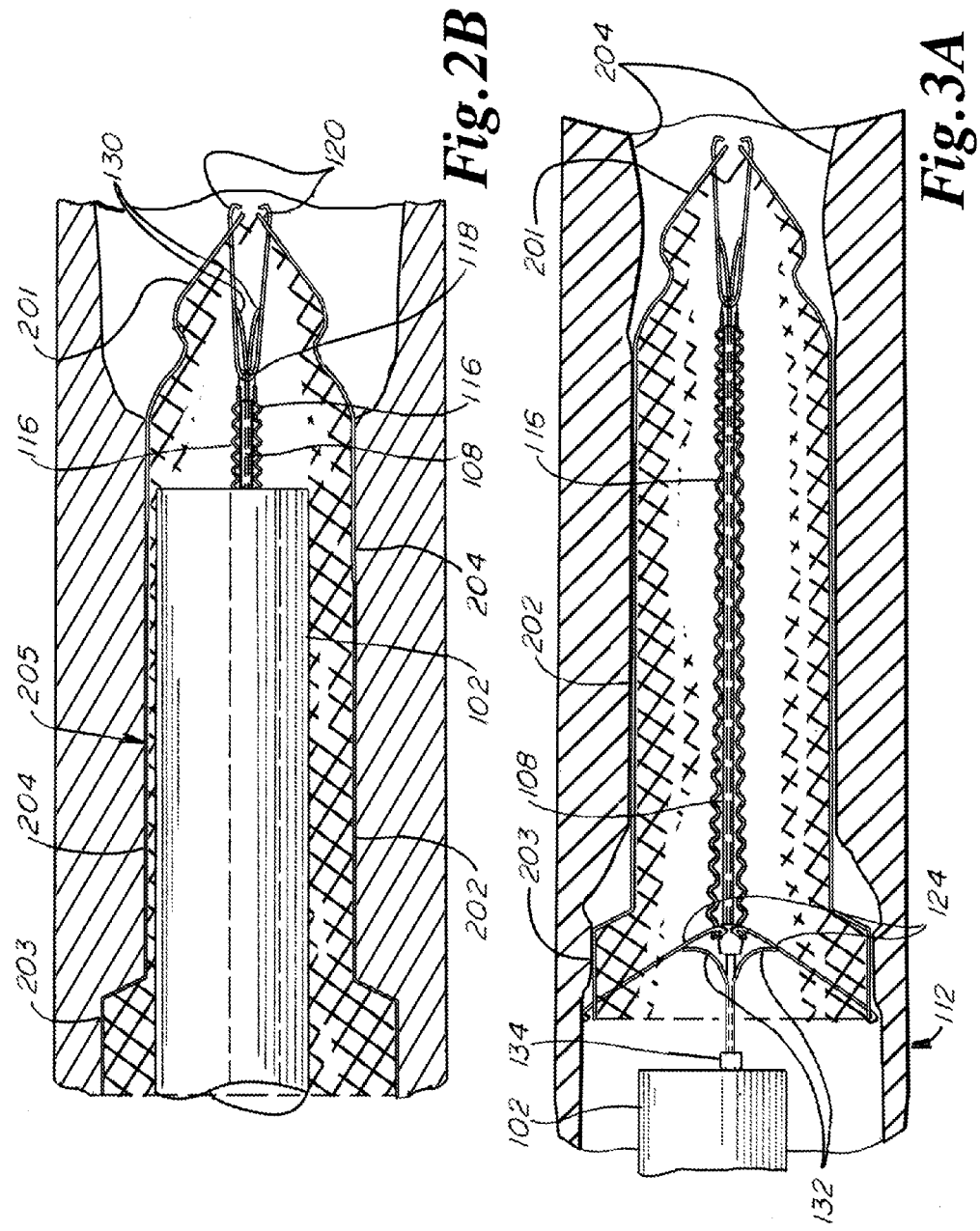

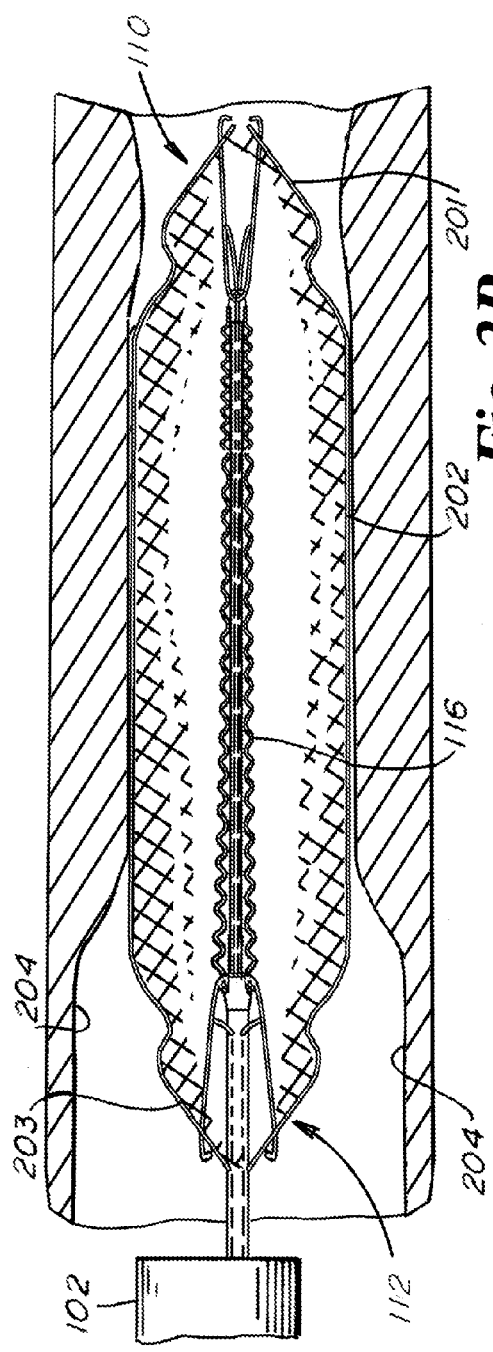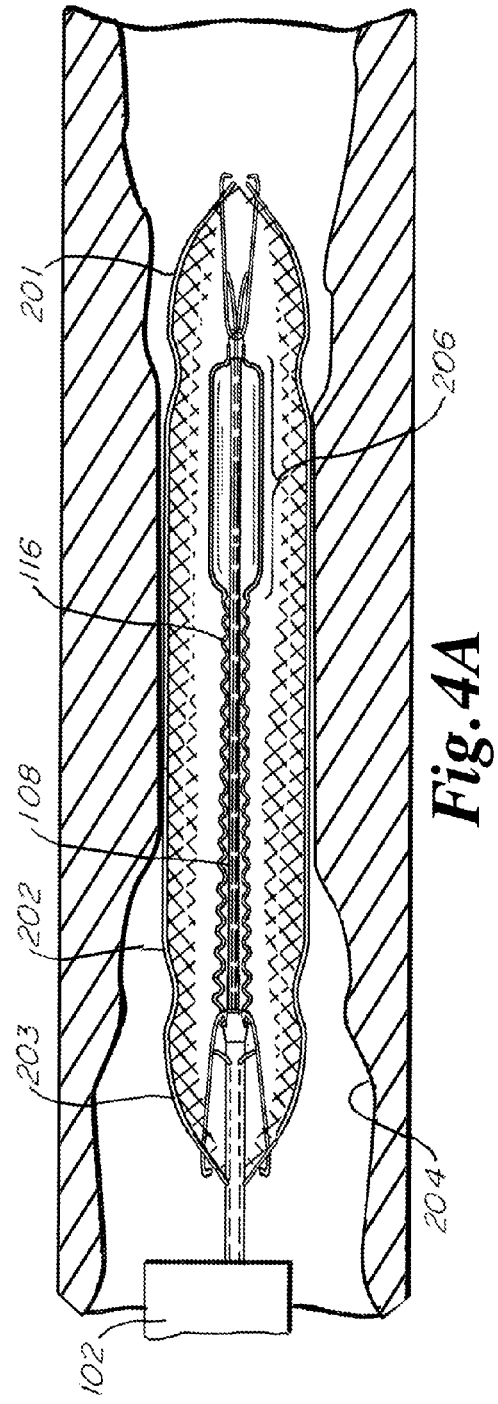

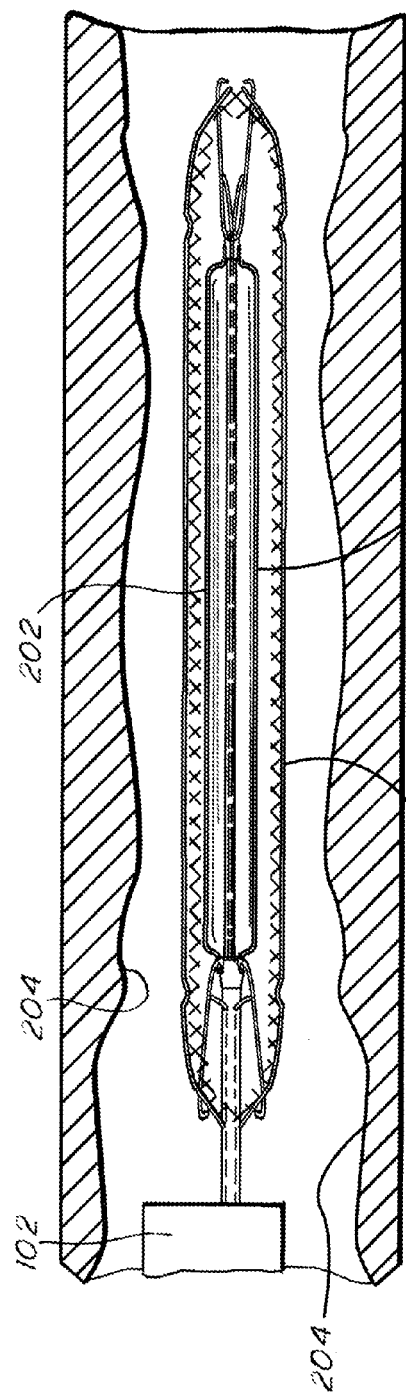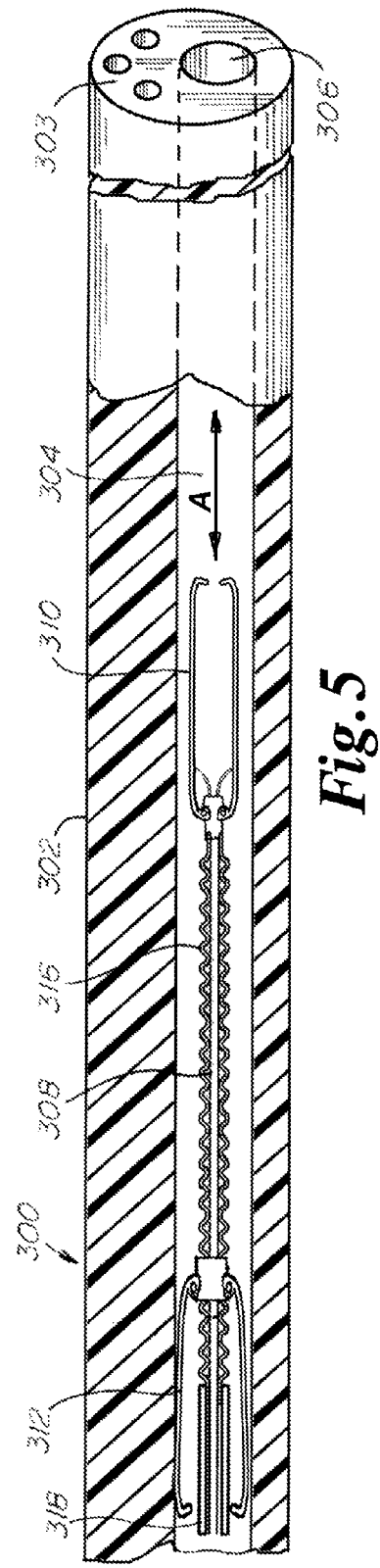
Fig.4B
Fig.5

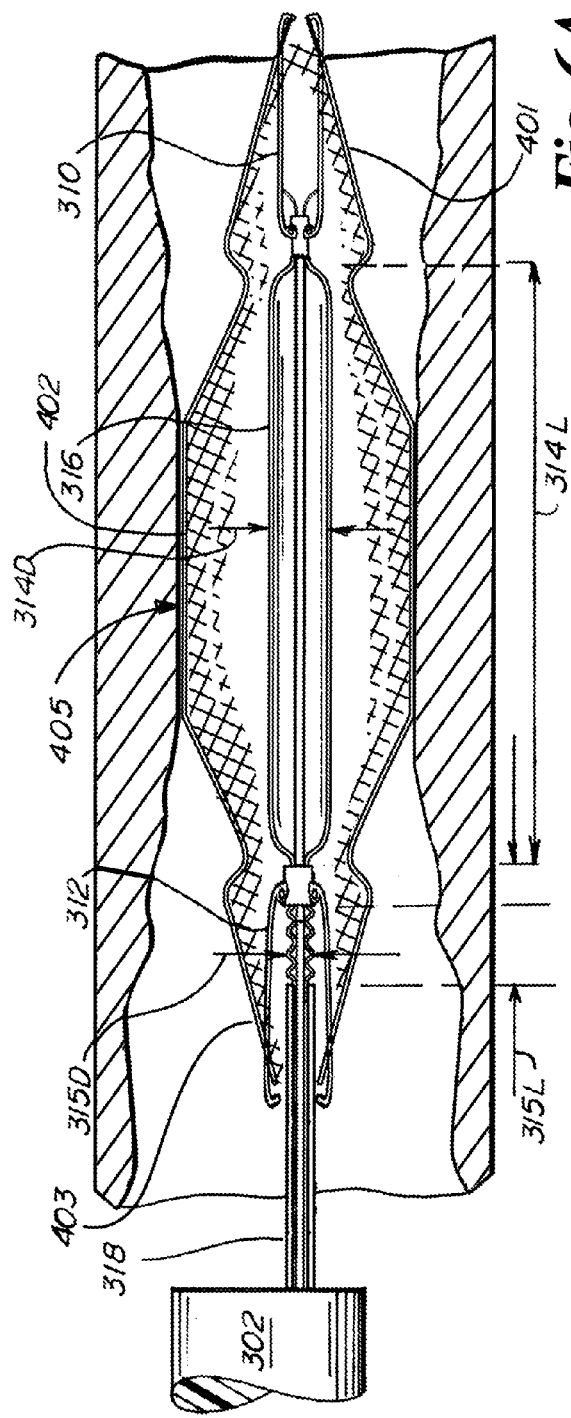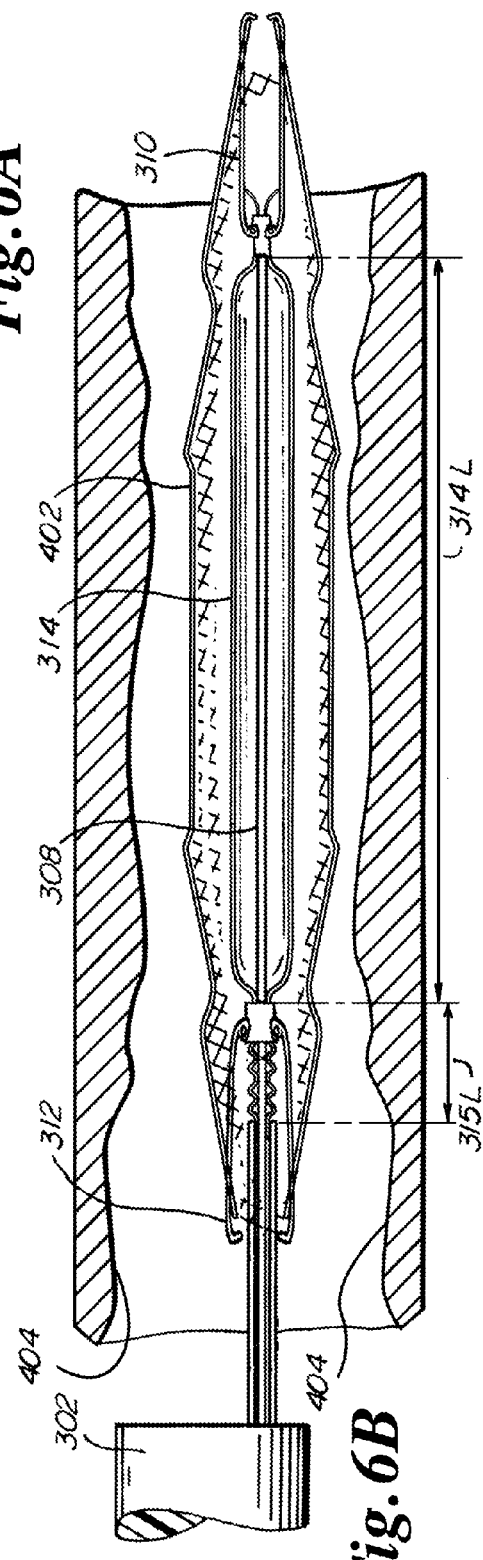

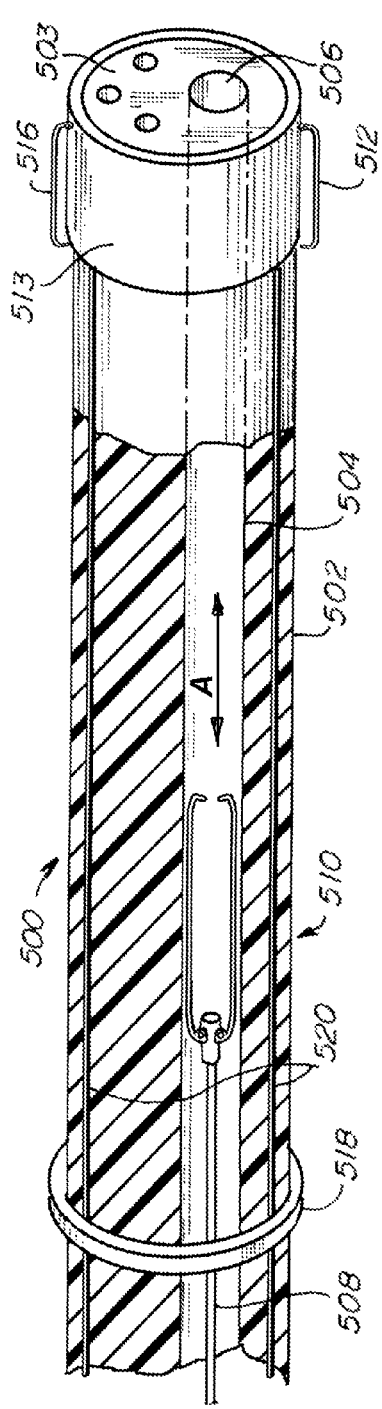
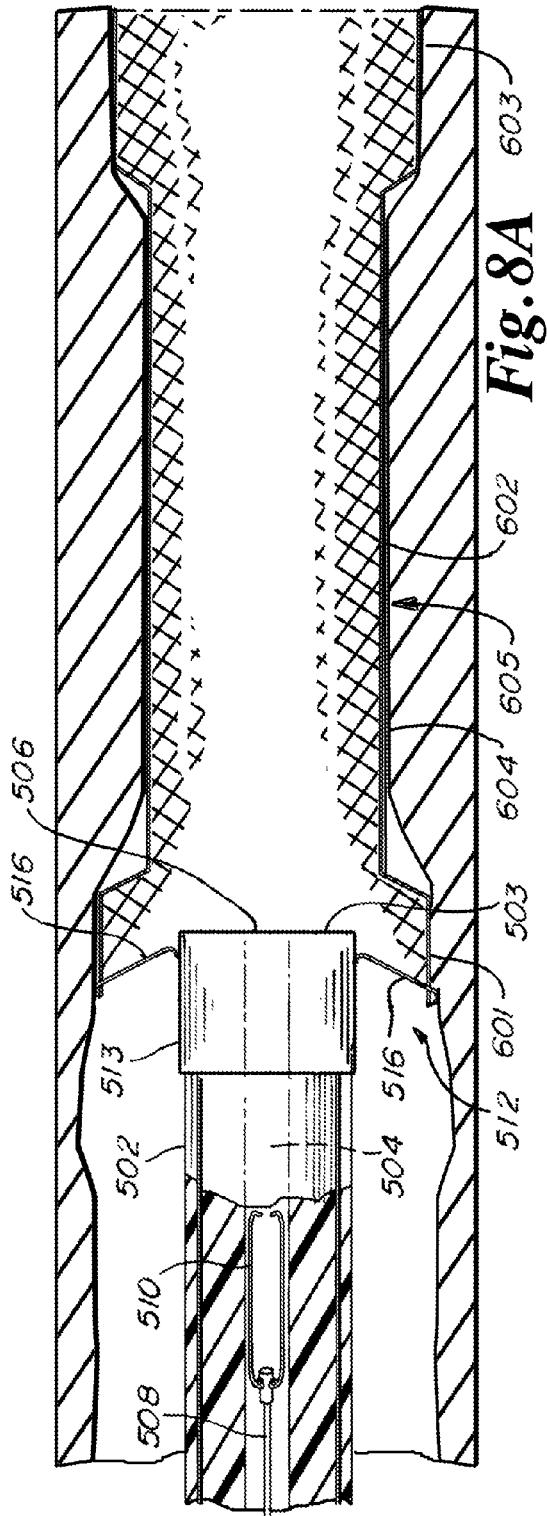

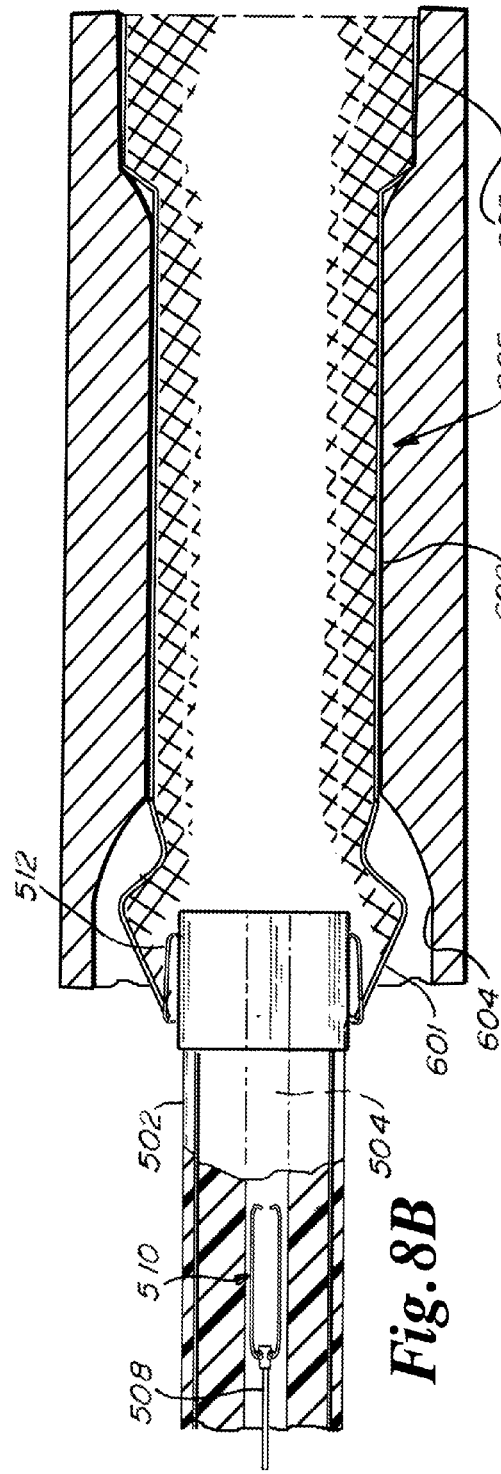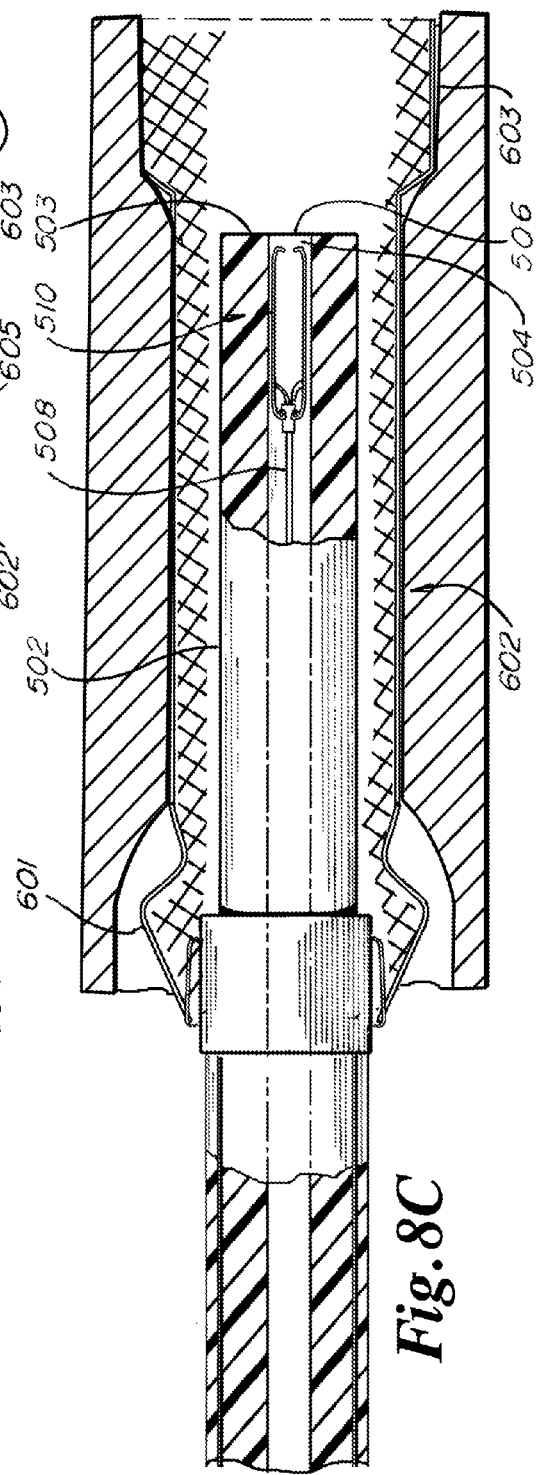

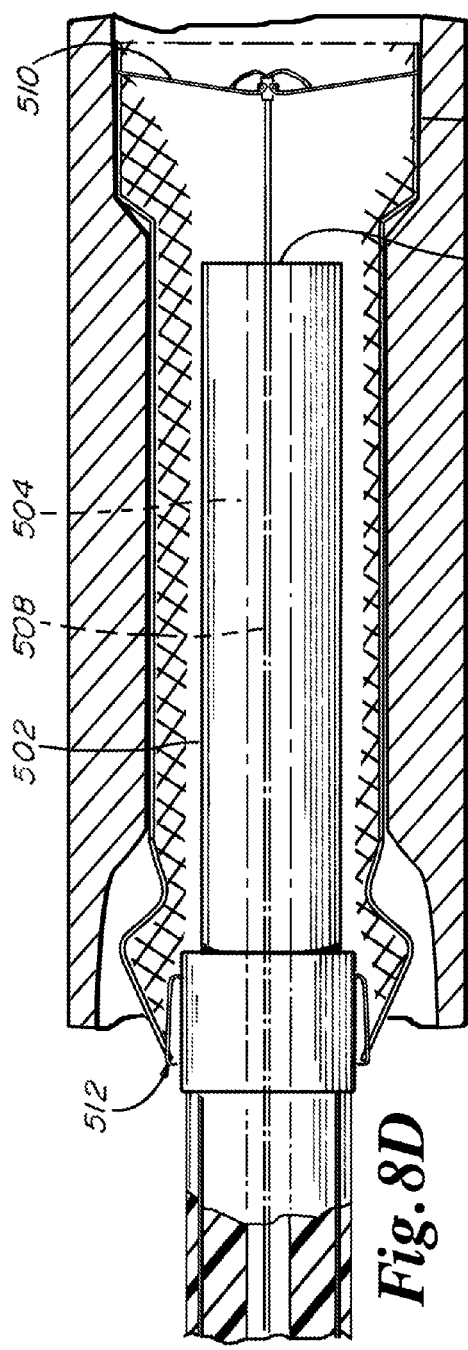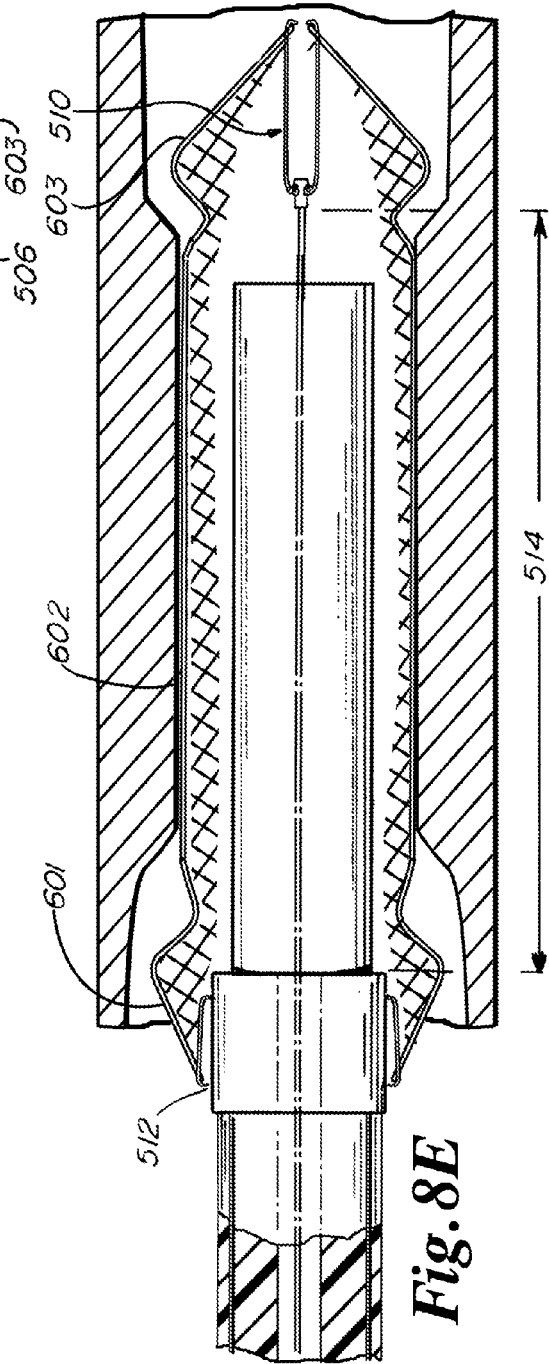

APPARATUSES FOR MANIPULATING MEDICAL DEVICES AND RELATED METHODS FOR USE

CROSS-REFERENCE TO RELATED APPLICATIONS

This application claims the benefit of and priority to U.S. Provisional Application Ser. No. 61/970,180, filed Mar. 25, 2014, the entire contents of which are herein incorporated by reference.

TECHNICAL FIELD

The present disclosure pertains to apparatuses, and methods for using the apparatuses. More particularly, the present disclosure pertains to apparatuses that can manipulate a collapsible medical device (e.g., a stent).

BACKGROUND

A stent is an example of a collapsible medical device used, for example, in the treatment of diseased body lumens. A stent is generally a longitudinal tubular device formed of biocompatible material, which may be useful to open and support various body lumens. For example, stents may be used in body vessels, such as in the coronary or peripheral vasculature, an esophagus, a trachea, bronchi, a colon, a biliary tract, a urinary tract, a prostate, a brain, as well as in a variety of other locations in the body. Collapsible medical devices may be implanted within a vessel to open and/or reinforce collapsed or partially occluded portions of the vessel lumen. While stents are foreign objects to the human body, they may be designed to remain within a body lumen for prolonged periods or even indefinitely.

A stent may have an open flexible construction that may allow the stent to be inserted through curved vessels. Furthermore, this construction may allow the stent to be configured in a radially compressed state during delivery and/or implantation. Once properly positioned adjacent the damaged vessel, the stent may be radially expanded so as to support and conform to the vessel wall. Radial expansion of the stent has been accomplished by inflation of a balloon attached to the stent. Some stents foreshorten when radially expanded and get longer when radially contracted. Some stents are self-expanding that radially expands it once deployed. Super-elastic materials and metallic shape memory materials have been used to form stents.

On occasion, it may be useful to retrieve or reposition a stent previously deployed in a body lumen. For example, a stent may be relocated during deployment or after deployment for any of a variety of reasons. For example, a stent may be relocated and/or removed after a procedure that calls for only temporary use of the stent.

Deployed stents have been removed from body lumens by capturing a proximal end of the stent with a tool, such as a biopsy forceps or other snare, and then pulling proximally to withdraw the stent. One problem with this method is that pulling or pushing a fully radially expanded stent through a body lumen can damage surrounding tissue and the stent itself.

There is a need for a reliable and effective apparatus, system, and method for manipulating, removing, and/or repositioning a collapsible medical device (e.g., a stent) that has already been deployed inside a lumen (e.g., a body lumen).

SUMMARY

In one or more embodiments, an apparatus for manipulating a collapsible medical device includes a sheath having a distal end. The sheath defines a sheath lumen extending axially through at least a portion of the sheath and terminates at a sheath distal opening. In one or more embodiments, the apparatus further includes a first shaft including a first grasping member. The first shaft is structured and arranged to slide axially within and relative to the sheath lumen from a delivery configuration to a first grasping configuration and optionally further to a second grasping configuration. In one or more embodiments, the apparatus also includes a second grasping member and a balloon. The second grasping member is structured and arranged to slide axially relative to the first shaft, the second grasping member separated from the first grasping member by a distance. In one or more embodiments, the balloon is expandable from an engaged configuration to an elongated configuration. In one or more embodiments, the balloon is structured and arranged such that expansion of the balloon changes the distance.

In one or more embodiments, an apparatus for manipulating a collapsible medical device includes a sheath having a distal end, a first shaft having a first grasping member, and a second grasping member. The sheath defines a sheath lumen extending axially through at least a portion of the sheath and terminates at a sheath distal opening. In one or more embodiments, the first grasping member is structured and arranged to slide axially relative to the sheath within the sheath lumen from a delivery configuration to a grasping configuration. In the delivery configuration, the first grasping member is disposed at least partially within the sheath lumen, whereas in the grasping configuration, the first grasping member is disposed distal of the sheath distal opening. In one or more embodiments, the second grasping member includes a tubular member that is disposed about the sheath and structured and arranged to slide axially relative to the sheath.

In another aspect of the present disclosure, a method of manipulating a collapsible medical device is provided. In one or more embodiments, the collapsible medical device has a distal portion, a proximal portion, and a medial portion disposed between the proximal and distal portions, and the collapsible medical device is extending longitudinally in an axial direction. In one or more embodiments, the method includes disposing an apparatus to the vicinity of the collapsible medical device, wherein the apparatus includes a sheath having a sheath lumen, a first grasping member, and a second grasping member. In particular, the first grasping member has a delivery configuration when disposed within the sheath lumen and a grasping configuration when disposed distal of the sheath lumen. In one or more embodiments, the method includes grasping the distal portion of the collapsible medical device with the first grasping member, for example, while at least a portion of the sheath is disposed within at least one of the distal portion, the medial portion, and the proximal portion of the collapsible medical device. In one or more embodiments, the method includes actuating the first grasping member to at least partially collapse the distal portion of the collapsible medical device. In one or more embodiments, the method includes grasping the proximal portion of the collapsible medical device with the second grasping member and actuating the second grasping member to at least partially collapse the proximal portion of the collapsible medical device. In one or more embodiments, the method further includes increasing the distance in the axial direction between the first and second grasping members, for example, to at least partially collapse at least a medial portion of the collapsible medical device disposed between the distal portion and the proximal portion.

The above summary of one or more embodiments is not intended to describe every disclosed embodiment or every implementation of the subject matter of the present disclosure. The drawings and detailed description, which follow, more particularly describe one or more embodiments of the present disclosure.

BRIEF DESCRIPTION OF THE DRAWINGS

A detailed description is hereafter provided with specific reference being made to the drawings.

FIGS. 2A-2B are partial cross-sectional views of the apparatus of FIG. 1, the apparatus in a first grasping configuration;

FIGS. 3A-3B are partial cross-sectional views of the apparatus of FIG. 1, the apparatus in a second grasping configuration;

FIGS. 4A-4B are partial cross-sectional views of the apparatus of FIG. 1 having a balloon in partially- and fully-inflated configurations, respectively;

FIG. 5 is a perspective view of an apparatus of at least one embodiment of the present disclosure, the apparatus in a delivery configuration;

FIGS. 6A-6B are partial cross-sectional views of the apparatus of FIG. 5 having a balloon in partially-inflated and further-inflated configurations;

FIG. 7 is a perspective view of an apparatus of at least one embodiment of the present disclosure, the apparatus in a delivery configuration; and FIGS. 8A-8F are partial cross-sectional views of the apparatus of FIG. 7.

Figure 1:
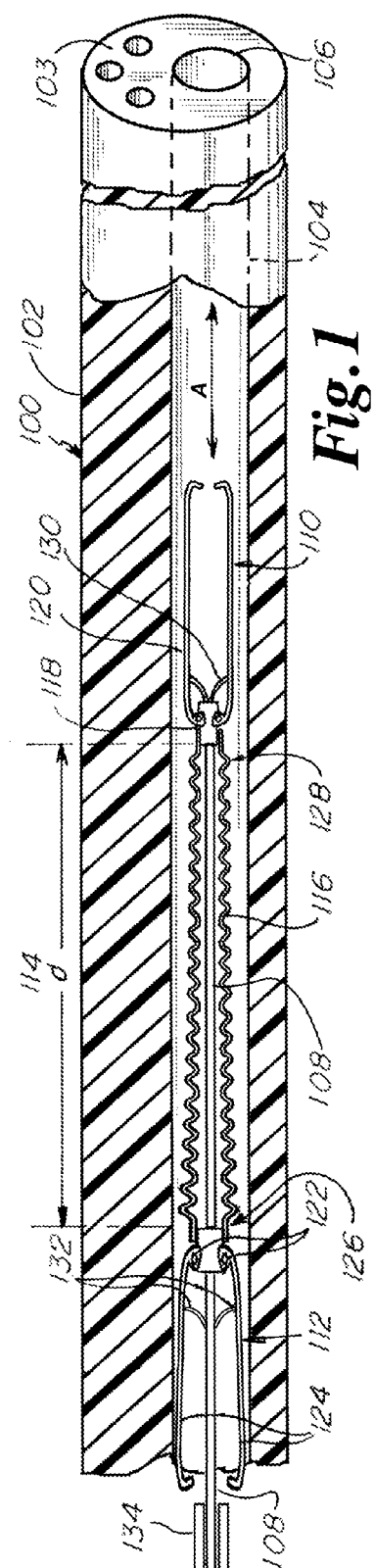
FIG. 1 is a perspective view of an apparatus of at least one embodiment of the present disclosure, the apparatus in a delivery configuration.

While the disclosure is amenable to various modifications and alternative forms, specifics thereof are shown by way of examples in the drawings and are described in detail. It should be understood, however, that the intention is not to limit the present disclosure to the particular embodiments described. On the contrary, the intention is to cover all modifications, equivalents, and alternatives falling within the scope of the present disclosure.

DETAILED DESCRIPTION

Definitions are provided for the following defined terms. It is intended that these definitions be applied, unless the context indicates otherwise.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used herein, the singular forms "a", "an", and "the" include plural references unless the context clearly indicates otherwise. As used herein, the term "or" is generally employed in its sense including "and/or" unless the context clearly indicates otherwise.

References herein to "an embodiment," "some embodiments," "other embodiments," etc., indicate that the embodiment described may include a particular feature, structure, or characteristic, but not every embodiment necessarily includes the particular feature, structure, or characteristic. Moreover, such phrases do not necessarily refer to the same embodiment. Further, when a particular feature, structure, or characteristic is described in connection with one embodiment (or more embodiments), it should be understood that such feature, structure, or characteristic may also be used in connection with other embodiments, whether or not explicitly described, unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

The present disclosure relates to apparatuses, devices, and methods for manipulating a collapsible medical device (e.g., a stent) that is, for example, disposed in a bodily passageway. The subject matter of the present disclosure may allow an operator (e.g., a clinician, physician, etc.) to remove or reposition a collapsible medical device while reducing or eliminating damage to the apparatus, the medical device, and/or the surrounding tissue. Applications of one or more embodiments of the apparatuses of the present disclosure include medical applications (particularly, endoscopic therapy) in, for example, the gastrointestinal tract, the biliary tract, the urinary tract, or the respiratory tract.

In particular, one or more embodiments of the present disclosure are directed to apparatuses and methods for manipulating and/or removing an intraluminary prosthesis, such as a stent, disposed within a body lumen. Reference herein to bodily passageways or lumens may refer to vessels or passageways in any of the aforementioned tracts and systems or elsewhere in the body. While discussed below primarily in connection with manipulating radially expanding stents, the apparatus and methods of the present disclosure can also be used to manipulate or remove other types of collapsible medical devices (e.g., stents, prostheses, stent-grafts, etc.). Additionally, in accordance with one or more embodiments of the present disclosure, the apparatus could also be used to remove other objects from within a body lumen.

It should be noted that references herein to the term "distal" are to a direction away from an operator, while references to the term "proximal" are to a direction towards the operator. Accordingly, when the terms "distal" and "proximal" are used herein in the context of an apparatus that is being deployed within a body, such as a human body, by an operator, the term "distal" refers to a location within the body that is farther within the body than a location that is "proximal" to the operator.

Referring now to the drawings, FIG. 1 shows an apparatus 100 for manipulating a collapsible medical device (not shown), in accordance with one or more embodiments of the present disclosure. In particular, apparatus 100 may be used for manipulating an intraluminal implant, such as a stent, that is disposed in a body lumen (not shown). However, it should be noted that apparatus 100 may also be employed to manipulate any of a wide variety of suitable intraluminal implants (e.g., a stent, a stent-graft, a shunt, etc.) or other medical devices.

The apparatus 100, shown in FIG. 1, includes a sheath 102, a first shaft 108 having a first grasping member 110 attached thereto, a second grasping member 112, and a balloon 116.

Apparatus 100 is shown, in FIG. 1, in a delivery configuration having first grasping member 110, second grasping member 112, and balloon 116 wherein first grasping member 110 is disposed at least partially (e.g., completely) inside a sheath lumen 104. In other words, in the delivery configuration, the distal end of first grasping member 110 is disposed proximal of sheath lumen opening 106 or is otherwise prevented from contacting a lumen wall while distal end 103 of sheath 102 is moved within a lumen. In the delivery configuration, apparatus 100 may have a profile of sheath 102 and may be inserted into and navigated through a lumen (e.g., a body lumen) while avoiding substantial (e.g., harmful) contact between the first grasping member and the lumen wall. In one or more embodiments, after the distal end of the sheath is positioned in a desired location/configuration within a lumen (e.g., body lumen, etc.), first grasping member 110 can be axially deployed from sheath 102 through sheath distal opening 106 to be in a first grasping configuration. In one or more embodiments, second grasping member 112 and balloon 116 can be axially deployed from sheath 102 through sheath distal opening 106 such that apparatus 100 is in a second grasping configuration. In one or more embodiments, a second grasping configuration includes second grasping member 112 being in a position to grasp a collapsible medical device (e.g., a stent, etc.). In one or more embodiments, apparatus 100, or portions thereof, can be used as part of or in conjunction with other endoscopic systems.

In one or more embodiments, apparatus 100 may be used, for example, in a method to manipulate (e.g., reposition, remove, etc.) a medical device, such as a stent. For example, FIGS. 2A-4B show the use of apparatus 100 for manipulating a stent 202 positioned within a lumen 204 (e.g., a body lumen, an esophagus wall, etc.). In one or more embodiments, sheath 102 is structured and arranged for entry into a body such that it can be navigated to a selected site in a body lumen. In one or more embodiments, sheath 102 is sufficiently flexible to bend to accommodate curved (e.g., serpentine, etc.) luminal passages and has sufficient axial stiffness to allow sheath distal end 103 to be moved along the lumen (e.g., to the site of a collapsible medical device) by operator control from a proximal end (not shown) of sheath 102.

In one or more embodiments, sheath 102 include or be may be formed from any one or more of a wide variety of biocompatible materials (e.g., biocompatible polymers, etc.). In one or more embodiments, a suitable biocompatible polymer includes, but is not limited to, polypropylene (PP), polytetrafluoroethylene (PTFE), polyethylene terephthalate (PET), high density polyethylene (HDPE), and the like. In one or more embodiments, sheath 102 has one or more layers, coverings, films, coatings, and the like (e.g., a polymeric covering), disposed over a sheath outer surface to affect interaction with the lumen wall (e.g., a body lumen wall) or disposed over a sheath inner surface to affect interaction with components moving along sheath lumen 104. In one or more embodiments, sheath 102 or one or more portions thereof can be, without limitation, transparent, opaque, translucent, colored, and/or non-transparent, as may be desired for a particular application.

In one or more embodiments, sheath 102 has a generally tubular configuration having, for example, a circular cross-sectional shape. It should be noted, however, that any suitable cross-sectional shape may be contemplated such as, but not limited to, a regular polygon (e.g., a rectangle, etc.), an irregular polygon, a curved shape (e.g., elliptical, etc.), an irregular shape, or the like. Sheath lumen 104 may extend axially through at least a portion of sheath 102 and terminates at a sheath distal opening 106. In one or more embodiments, first grasping member 110, second grasping member 112, and balloon 116 are moved through sheath lumen 104 and may pass through sheath distal opening 106. In one or more embodiments, sheath lumen 104 extends axially through the entire length of sheath 102. In one or more embodiments, sheath lumen 104 extends through only a partial length of sheath 102. Although not fully shown in FIG. 1, sheath 102 may, in one or more embodiments, include a plurality of sheath lumens, each of which may have similar form and function as that of sheath lumen 104.

In one or more embodiments, first grasping member 110 is coupled (e.g., attached, adhered, connected, etc.) to first shaft 108 near its distal end (not shown). First shaft 108 defines a flexible and axially-resilient structure (e.g., a tubular structure, etc.). First shaft 108 may be configured to slide axially within and relative to sheath lumen 104. In one or more embodiments, first shaft 108 has a generally tubular configuration having, for example, a circular cross-section shape. It should be noted, however, that any suitable cross-sectional shape may be contemplated such as, but not limited to, a regular polygon (e.g., a rectangle, etc.), an irregular polygon, a curved shape (e.g., an ellipse, etc.), an irregular shape, or the like.

In one or more embodiments, first shaft 108 may include or be formed from any of a wide variety of biocompatible materials such as, but not limited to, a metal, an alloy, a polymer, and combinations of more than one of any of these. In one or more embodiments, the material of first shaft 108 is compatible with that of sheath 102 in a manner that first shaft 108 may be moved through sheath lumen 104. In one or more embodiments, first shaft 108 has sufficient rigidity (e.g., column strength) to be moved through sheath lumen 104 by, for example, pushing from the proximal end of the first shaft 108, and has sufficient flexibility to move through sheath lumen 104 and follow sheath 102 through curved (e.g., tortuous) pathways while reducing or avoiding damage to the inner wall of sheath lumen 104.

FIGS. 1-4B also show various positioning of first grasping member 110 in accordance with the present disclosure. In one or more embodiments, first grasping member 110 forms a distally diverging or expanding structure that is configured to grasp a collapsible medical device (e.g., a distal portion thereof, etc.), such as a stent, for manipulation (e.g., removal, repositioning, etc.).

Figure 2A:
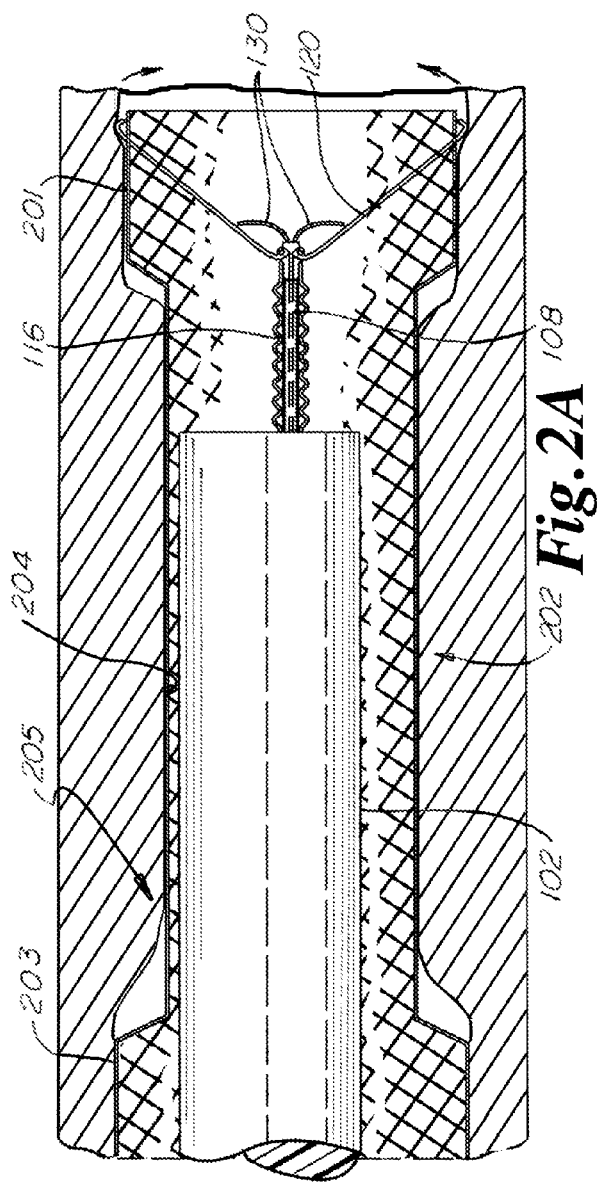

In one or more embodiments, first grasping member 110 includes one or more (e.g., a pair) jaws 120 configured to pivot about a hinge 118. One or more jaws 120 may pivot about hinge 118 to switch between a closed state and an open state. For example, in FIG. 1, first shaft 108 having first grasping member 110 attached thereto is shown in a delivery configuration wherein first grasping member 110 is disposed within sheath lumen 104 having, for example, two jaws 120 in at least a partially closed state. In FIG. 2A, first shaft 108 is at least partially extending out of sheath lumen 104 and includes two jaws 120 at least partially opened so as to grasp at least a portion (e.g., distal portion) of collapsible medical device 202 (e.g., stent) disposed within lumen wall 204 (e.g., esophagus wall, etc.).

In one or more embodiments, first grasping member 110 is structured and arranged to fit inside sheath 102 when in the delivery configuration and capable of pivoting to reach and grasp a collapsible medical device when in a first grasping configuration. In one or more embodiments, first grasping member 110 can be axially moved beyond sheath distal opening 106, thus allowing two jaws 120 (e.g., FIG. 2A, etc.) to expand and diverge to form a forceps-shaped structure. In one or more embodiments, a first grasping member may include a forceps.

In one or more embodiments, apparatus 100 includes a second shaft 134 having a second grasping member 112 coupled adjacent its distal end (e.g., FIG. 1). Second shaft 134 may include a lumen (not shown) through which first shaft 108 may extend and slide relative thereto. In one or more embodiments, the inner diameter of second shaft 134 (e.g., the diameter of a lumen defined by second shaft 134) is dimensioned such that first shaft 108 may extend and slide therein (e.g., in a frictional or frictionless engagement). In one or more embodiments, second grasping member 112 is similar in form and function to that of first grasping member 110. For example, as shown in FIG. 3A, second grasping member 112 includes one or more (e.g., a pair) jaws 124 configured to pivot about a hinge 122, similar to that of first grasping member 110. In one or more embodiments, the second grasping member 112 includes jaws 124 that open proximally, whereas first grasping member 110 includes jaws 120 that open distally. Jaws 124 may pivot about hinge 122 to switch between a closed state and an open state. For example, in FIG. 1, second grasping member 112 is shown with two jaws 124 in the closed state, whereas second grasping member 112 is shown in the open state in FIG. 3A, wherein opened jaws 124 of second grasping member 112 are adapted to grasp at least a portion (e.g., a proximal portion) of collapsible medical device 202 disposed within a lumen wall 204.

As shown in FIG. 2A, after each of two jaws 120 engages with the distal portion of the stent 202, control wires 130 may be pulled proximally relative to sheath 102 and first shaft 108 (e.g., while maintaining sheath 102 and first shaft 108 in place), causing jaws 120 to close, as illustrated in FIG. 2B. As a result, distal portion 201 of stent 202 radially contracts (e.g., collapses), to facilitate breaking of the engagement (e.g., tissue interlock) between stent 202 and lumen wall 204 (e.g., esophagus wall).

In one or more embodiments, balloon 116 is mounted on first shaft 108 having a proximal portion 126 coupled to second grasping member 112 and a distal portion 128 coupled to first grasping member 110. As shown in FIG. 1, balloon 116 has a length 114 that dictates the distance between first grasping member 110 and second grasping member 112. In one or more embodiments, balloon 116 is structured and arranged such that its expansion changes its length 114. As a result, distance 114 between first grasping member 110 and second grasping member 112 also changes upon further inflation. In one or more embodiments, length 114 of balloon 116 is approximately equal to the length of a collapsible medical device 202 (e.g., stent) that is deployed within a lumen such that, upon inflation of balloon 116, length 114 increases. In one or more embodiments, length 114 of balloon 116 is either smaller or greater than that of collapsible medical device 202. In one or more embodiments, balloon 116, along with the grasping configurations of the two grasping members 110 and 112, provides a structure to disengage (e.g., partially, completely, etc.) a collapsible medical device from a lumen.

In one or more embodiments, balloon 116 is structured and arranged to expand between an engaged configuration and an elongated configuration. In the engaged configuration, balloon 116 may be coupled to and disposed between first grasping member 110 and second grasping member 112, wherein both first grasping member 110 and second grasping member 112 are respectively engaging (e.g., grasping, radially contracting, collapsing, etc.) distal and proximal portions (e.g., ends, etc.) of a collapsible medical device. In the present disclosure, in the engaged configuration, balloon 116 is sufficiently deflated such that balloon 116 does not urge first grasping member 110 away from second grasping member 112 as a consequence of the balloon's extent of inflation. That is, further deflation of balloon 116 from an engaged configuration might not itself result in decreasing the distance between first grasping member 110 and second grasping member 112. In contrast, in the elongated configuration of balloon 116, balloon 116 is sufficiently inflated such that balloon 116 urges (e.g., applies a force against, etc.) first grasping member 110 and second grasping member 112 in opposite axial directions.

For example, as shown in FIG. 2A, in the engaged configuration, balloon 116 is coupled to each of first grasping member 110 and second grasping member 112, each of which is respectively contracting (e.g., radially contracting, etc.) a proximal and a distal portion of a collapsible medical device. As shown in FIG. 2A, each of the proximal portion and the distal portion of the collapsible medical device is disengaged from the lumen wall. In such a configuration, the collapsible medical device may be disengaged from the surrounding lumen wall (e.g., body lumen wall, etc.) at the proximal and distal portions while a medial portion of the collapsible medical device, located between the proximal and distal portions, may be in contact with the surrounding lumen wall. In one or more embodiments, balloon 116 is inflated (e.g., partially inflated, fully inflated) into an elongated configuration, thereby urging first grasping member 110 away from second grasping member 112. In one or more embodiments, urging first grasping member 110 away from second grasping member results in contraction (e.g., radial contraction) of the medial portion of the collapsible medical device, which may result in partially or completely disengaging the medial portion of the collapsible medical device from the surrounding lumen wall.

FIGS. 2A-4B illustrate one or more methods of using apparatus 100 to manipulate a collapsible medical device 202, such as a stent, engaged with an lumen wall 204 (e.g., an esophagus wall). In one or more embodiments, sheath 102 is advanced to the site of, for example, a deployed collapsible medical device 202. During advancement of sheath 102, first grasping member 110 may be at least substantially retracted, disposed within sheath lumen 104. In one or more embodiments, first grasping member 110 is advanced in the distal direction relative to the sheath by, for example, moving first shaft 108 in the distal direction relative to sheath 102. For example, an operator may push first shaft 108 toward a target region while pulling or holding stationary a sheath handle. Alternatively, the sheath handle may be moved proximally, while pushing or holding stationary first shaft 108. The result of relative axial movement between first grasping member 110 and sheath 102 is that first grasping member 110 is positioned distal of the sheath lumen opening (e.g., adjacent the target region, adjacent a distal portion 201 of the stent 202, etc.).

As shown in FIG. 2A, in the first grasping configuration, the one or more jaws 120 of first grasping member 110 are aligned with stent 202 such that first grasping member 110 engages a distal portion of stent 202. The one or more jaws 120 may be actuated (e.g., pivoted, rotated, etc.) about hinge 118 using one or more control wires 130, as shown in FIG. 1. In one or more embodiments, each control wire 130 is operably coupled to one or more jaws 120 such that pulling and/or pushing an individual control wire 130 closes and/or opens one or more jaws 120, respectively.

As shown in FIG. 2A, after each of two jaws 120 engages with the distal portion of the stent 202, control wires 130 may be pulled proximally relative to sheath 102 and first shaft 108 (e.g., while maintaining sheath 102 and first shaft 108 in place), causing jaws 120 to close, as illustrated in FIG. 2B. As a result, distal portion 201 of stent 202 radially contracts (e.g., collapses), to facilitate breaking of the engagement (e.g., tissue interlock) between stent 202 and lumen wall 204 (e.g., esophagus wall).

In one or more embodiments, second shaft 134 may be moved in the distal direction relative to sheath 102 (e.g., while holding a sheath handle (not shown) stationary). Alternatively, the sheath handle could be moved proximally relative to second shaft 134 (e.g., while holding second shaft 134 stationary). The result of the relative axial movement between second grasping member 112 and sheath 102 is that second grasping member 112 is positioned distal of the sheath lumen opening (e.g., adjacent the target region, adjacent a proximal portion 203 of stent 202, etc.).

As shown in FIG. 3A, in the second grasping configuration, the one or more jaws 124 of second grasping member 122 are aligned with stent 202 such that second grasping member 112 engages a proximal portion 203 of stent 202. In one or more embodiments, the one or more jaws 124 are actuated (e.g., pivoted, rotated, etc.) about hinge 122 using one or more control wires 132, as shown in FIG. 1. In one or more embodiments, each control wire 132 is operably coupled to the one or more jaws 124 such pulling and/or pushing an individual control wire 132 closes and/or opens one or more jaws 124, respectively.

As shown in FIG. 3A, after each of two jaws 124 engages with proximal portion 203 of stent 202, control wires 132 may be pulled proximally relative to sheath 102 and second shaft 134 (e.g., while maintaining sheath 102 and second shaft 134 in place), causing jaws 124 to close, as illustrated in FIG. 3B. As a result, proximal portion 203 of stent 202 radially contracts (e.g., collapses), to facilitate disengagement (e.g., tissue interlock) between stent 202 and lumen wall 204 (e.g., the surrounding tissue of an esophagus wall).

In one or more embodiments, a collapsible medical device includes one or more portions (e.g., one or more end portions) that protrude radially inward to a sufficient extent that grasping the protrusion may be accomplished with, for example, increased reliability and/or reduced trauma to the lumen wall. For example, some stents include one or more end loops that, even in a fully deployed configuration, tend to deflect radially inwardly. The difficulty of grasping a collapsible medical device may be reduced by snagging one of these end loops or a similar deflecting end portion with a grasping member, such as first grasping member 110 and/or second grasping member 112.

In one or more embodiments, removing collapsible medical device 202 includes disengaging a medial portion 205 of collapsible medical device 202, as shown in FIGS. 4A-4B. In FIGS. 4A and 4B, balloon 116 is inflated while having its distal portion 128 coupled to first grasping member 110 and its proximal portion 126 coupled to second grasping member 112. Initially, a portion 206 of balloon 116 is inflated, as shown in FIG. 4A. As shown, portion 206 is disposed adjacent distal portion 201 of stent 202, as a result, a portion of stent 202 is disengaged at its distal portion 201. In one or more embodiments, further inflating (e.g., fully inflating) balloon 116 elongates balloon 116, which radially contracts (e.g., collapses) stent 202 to completely disengage stent 202 (see FIG. 4B) from lumen wall 204 (e.g., surrounding tissue, an esophagus wall). In one or more embodiments, expansion of balloon 116 causes an increase in the distance separating first grasping member 110 and second grasping member 112. In the present disclosure, balloon 116 may be inflated using any suitable inflation fluid, such as, but not limited to, water, saline, air, etc. In the present disclosure, the volume of inflation medium in balloon 116 is greater in the elongated configuration than in the engaged configuration.

By lengthening collapsible stent 202, the radial profile of stent 202 decreases such that stent 202 can be moved out of the lumen, by, for example, drawing stent 202 within sheath lumen 106. Stent 202 may be re-positioned at a different location or may be removed from the lumen (e.g., body lumen) via any appropriate means. For example, stent 202 in the collapsed state (e.g., stent's medial portion has a diameter less than the diameter of sheath lumen 106, etc.) may be retracted into sheath 102 with balloon 116 inflated having first grasping member 110 and second grasping member 112 holding stent 202 at its distal portion 201 and proximal portion 203. In one or more embodiments, at least a distal portion of second shaft 134 is drawn into sheath 102 such that apparatus 100 can be moved proximally within lumen 204. In one or more embodiments, stent 202 along with first grasping member 110 and second grasping member 112 could also be fully drawn into sheath 102 for removal from the body lumen. In one or more embodiments, sheath 102 may be retracted from a patient's body, where the grasping members may be opened to release the stent.

In another aspect of the present disclosure, FIGS. 5-6B illustrate one or more embodiments of an apparatus for manipulating a collapsible medical device. Apparatus 300 includes a sheath 302, a first grasping member 310, a second grasping member 312, and a balloon 316 similar in form and function as that of sheath 102 and other said components as described in FIGS. 1-4B. In contrast to one or more embodiments discussed in FIGS. 1-4B, second grasping member 312 in FIGS. 5-6B is moveably disposed around deflated balloon 316. In particular, second grasping member 312 is mounted on balloon 316 between the balloon's proximal end and distal end. As shown in FIG. 5, a proximal portion of balloon 316 may be operably coupled to a second shaft 318 similar to second shaft 134 of FIG. 1, whereas a distal portion of balloon 316 is coupled to first grasping member 310. As depicted in FIG. 5, balloon 316 has a first portion 314 disposed between first grasping member 310 and second grasping member 312, wherein first portion 314 has a first length 314L and a first diameter 314D. Balloon 316 may also include a second portion 315 proximal of second grasping member 312 having a second length 315L and a second diameter 315D.

Although not explicitly shown, each of first grasping member 310 and second grasping member 312 may be moved distal of sheath lumen opening 306 in the same or similar manner as described with respect to FIG. 2A-3B. For example, after initially advancing sheath 302 to a target site (e.g., within lumen wall 404) of a deployed stent 402, grasping members may be fully or at least substantially retracted within sheath lumen 304. In one or more embodiments, first shaft 308 can be moved in the distal direction relative to sheath 302 (e.g., while holding a sheath handle (not shown) stationary), toward a target region. Alternatively, the sheath handle may be moved proximally relative to first shaft 308 (e.g., while holding first shaft 308 stationary). Either way, the result of relative axial movement between sheath 302 and first shaft 308 (e.g., first grasping member 310) is that first grasping member 310 and second grasping member 312 are positioned adjacent the target region (e.g., adjacent distal portion 401 and proximal portion 403 of stent 402). After the stent is grasped by first grasping member 310 and second grasping member 312, as shown in FIGS. 6A-6B apparatus 300 can manipulate a collapsible medical device 402 (e.g., stent). For example, in the same or similar manner as described with respect to FIG. 2A-3B, each of first grasping member 310 and second grasping member 312 may be actuated via one or more control wires to respectively grasp (e.g., radially contract, etc.) a distal portion of a stent 402 and a proximal end of stent 402. In one or more embodiments, after first grasping member 310 and second grasping member 312 are at or near the target region, either sheath 302 is retracted or first grasping member 310 and second grasping member 312 are pushed and actuated to deploy them in the first and second grasping configurations, respectively. In the second grasping configuration, each jaw of the respective grasping members are aligned with stent 402 such that first grasping member 310 and second grasping member 312 engage distal portion 401 and proximal portion 403 of stent 402, respectively. Similar to the embodiments discussed previously, each grasping member may include one or more jaws (e.g., a pair of jaws) and a hinge such that the one or more jaws are actuated (e.g., pivoted, rotated, etc.) about the hinge using, for example, one or more control wires. Each control wire operably couples to the one or more jaws such that the control wires may be pulled and/or pushed to close and/or open the one or more jaws, respectively.

As shown in FIG. 6A, after each of the two grasping members engage with (e.g., grab) distal portion 401 and proximal portion 403 of stent 402, control wires can be pulled proximally relative to sheath 302 and first shaft 308 (e.g., while maintaining sheath 302 and first shaft 308 in place), causing the one or more jaws of each grasping member to close, as illustrated in FIG. 6B. As a result, each of distal portion 401 and proximal portion 403 of stent 402 radially contracts (e.g., collapses) to facilitate disengagement (e.g., tissue interlock) between stent 402 and lumen wall 204 (e.g., the surrounding tissue of an esophagus wall).

In one or more embodiments, balloon 316 may be inflated while having its distal portion engaged with the first grasping member 310 and a middle portion engaged with the second grasping member 312. For example, balloon 316 can be expanded and/or inflated to a first partially expanded configuration and a second partially expanded configuration. In the first partially expanded configuration, first portion 314 of balloon 316 is inflated such that first diameter 314D of first portion 314 becomes greater than second diameter 315D of second portion 315. It should be noted that while first portion 314 of balloon 316 is inflated, the balloon may expand to a second partially expanded configuration where second length 315L of second portion 315 decreases as compared to second length 315L in first partially expanded configuration. In one or more embodiments, second grasping member 312 is structured and arranged to slide on the leading edge of the balloon inflation as balloon 316 is being inflated, thereby increasing the distance between first grasping member 310 and second grasping member 312. In this manner, as balloon 316 is further inflated, more of the balloon will be located between first grasping member 310 and second grasping member 312.

In one or more embodiments, first portion 314 is inflated (e.g., fully inflated) to increase the distance between first grasping member 310 and second grasping member 312 sufficiently to elongate the stent 402 such that medial portion 405 of stent 402 may radially contract (e.g., collapse). In one or more embodiments, radial contraction of stent 402 may completely disengage stent 402 from lumen wall 404 (e.g., from the surrounding tissue), as shown in FIG. 6B.

Figure 8F:
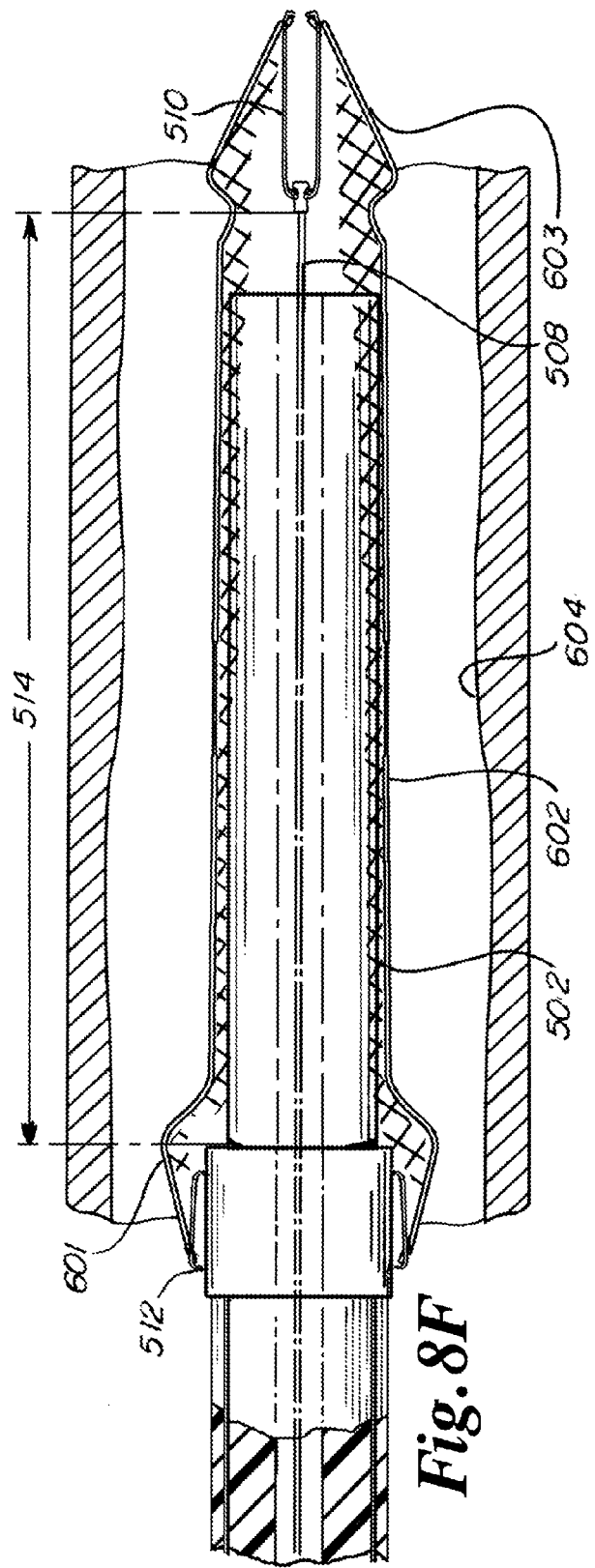

In another aspect of the present disclosure, FIGS. 7-8F illustrate one or more embodiments of an apparatus for manipulating a collapsible medical device. As shown in FIG. 7, apparatus 500 includes a sheath 502, a first grasping member 510, and a second grasping member 512. As shown in FIG. 7, sheath 502 has a distal end 503 and a sheath lumen 504 extending through at least a portion of sheath 502 and terminating at a sheath distal opening 506.

Apparatus 500 also includes a first shaft 508 having first grasping member 510 coupled to its distal portion. In one or more embodiments, first shaft 508 is configured to switch between a delivery configuration and a first grasping configuration, wherein first grasping member 510 is disposed at least partially within sheath lumen 504 in the delivery configuration as shown in FIGS. 7-8C and wherein first grasping member 510 is disposed distal of sheath distal opening 506 in the first grasping configuration as shown in FIGS. 8D-8F. In one or more embodiments, first grasping member 510 includes one or more jaws (e.g., a pair of jaws) and a hinge similar in form and function to that of first grasping members 110 and 310 as discussed in FIGS. 1-6B.

As shown in FIG. 7, second grasping member 512 includes a tubular member 513 that is disposed (e.g., slidably disposed, etc.) about sheath 502. In one or more embodiments, tubular member 513 is operably coupled to an outer surface of sheath 502 at or near sheath distal end 503. Tubular member 513 may be structured and arranged to slide axially relative to sheath 502.

In some embodiments, tubular member 513 is an endoscope cap or similar medical device. However, it should be understood that any suitable tubular member 513 coupled with, for example, a biopsy tool, a pair of rat-tooth forceps, or the like, may be employed. For example, sheath 502 may be an endoscope having sheath lumen 504 as a working channel of the endoscope.

In FIG. 8A, tubular member 513 has a generally cylindrical shape and is coupled to sheath 502 at the sheath distal end 503. Tubular member 513 may include one or more (e.g., a pair) jaws 516 coupled thereto, such that jaws 516 are configured to extend radially outwards to grasp a collapsible medical device and then radially inwards into a second grasping configuration. In one or more embodiments, tubular member 513 in a delivery configuration has jaws 516 aligned generally parallel along an axial direction A of sheath 502. In one or more embodiments, this is the configuration when sheath 502 is introduced and/or navigated through cavity lumen to reduce or avoid undesirable interaction of jaws 516 with the lumen wall. In one or more embodiments, after tubular member 513 is disposed in a target region (e.g., near stent 602), tubular member 513 can be shifted to the second grasping configuration by grabbing a portion of a stent 602, as shown in FIG. 8A, and actuating the second grasping members to disengage proximal end 601 of stent 602 from lumen wall 604, as shown in FIG. 8B.

In one or more embodiments, apparatus 500 includes one or more control wires (not shown) that are coupled to second grasping member 512 at one end and, for example, to a control mechanism (e.g., a handle, etc.) at a proximal end (e.g., near the operator, outside the lumen, etc.). Pushing and/or pulling the control wires may be done to actuate second grasping member 512, thereby switching it between, for example, the delivery configuration (e.g., FIG. 7) and the second grasping configuration (e.g., FIG. 8B). In one or more embodiments, to obtain the second grasping configuration, jaws 516 of tubular member 513 are extended radially outward to grab proximal portion 601 of stent 602 and extended radially inward to radially contract proximal portion 601 of stent 602.

As shown in FIG. 7, apparatus 500 includes a stopper 518 disposed proximal of tubular member 513. Stopper 518 may be structured and arranged to obstruct sliding of tubular member 513 beyond stopper 518 in the proximal direction. As shown in FIG. 7, the stopper may be mounted on sheath 502. In one or more embodiments, apparatus 500 includes a pull mechanism 520 (e.g., one or more strings, wires, etc.) that guide tubular member 513 toward stopper 518 until tubular member 513 contacts stopper 518. It should be noted that pull mechanism 520 may include any suitable device such as pull wires, or the like, and may be structured and arranged to push tubular member 513 in a distal direction (e.g., to sheath distal end 503).

In one or more embodiments, apparatus 500 includes first grasping member 510 retracted within sheath lumen 504 and fully contained within sheath 502 (see FIG. 7). In order to further engage stent 602, sheath 502 may be moved distally relative to lumen wall 604 (and relative to second grasping member 512 that may be engaging proximal portion 601 of stent 602) to dispose tubular member 513 proximal to the target region (e.g., adjacent distal portion 603 of stent 602), where first grasping member 510 may be switched to the first grasping configuration, as shown in FIG. 8E.

In one or more embodiments, first shaft 508 is advanced through sheath lumen 504 to move first grasping member 510 toward sheath distal opening 506, as shown in FIG. 8C. Further advancement of first shaft 508 will allow first grasping member 510 to exit sheath 502 through sheath distal opening 506 to a location proximal to distal end 603 of stent 602. Switching first grasping member 510 to the first grasping configuration may be accomplished in one or more embodiments, as shown in FIG. 8E, by causing one or more jaws of first grasping member 510 to extend radially outward to grab distal portion 603 of stent 602 and to extend radially inward to radially contract distal portion 603. For example, two jaws of first gasping member 510 are shown to grab distal portion 603 of stent 602 in FIGS. 8D-8E. In one or more embodiments, this can be accomplished by manipulating, for example, control wires connected to the jaws of first grasping member 510, similar to the one or more other embodiment described herein.

Tubular member 513 is now pulled proximally along the length of sheath 502 (and/or sheath 502 may be advanced through tubular member 513) till tubular member 513 meets stopper 518 at a proximal location. As a result, proximal portion 601 of stent 602 may be disengaged from lumen wall 604 (e.g., the surrounding tissue), as shown in FIG. 8B.

In one or more embodiments, after distal portion 603 of stent 602 is disengaged from lumen wall 604, first grasping member 510 can be pushed distally relative to second grasping member 512 along axial direction A of sheath 502, in order to at least partially radially contract stent 602. In one or more embodiments, second grasping member 512 can be pulled proximally relative to first grasping member 510 along axial direction A of sheath 502, in order to at least partially radially contract stent 602. In one or more embodiments, first shaft 508 and first grasping member 510 connected thereto may be moved distally relative to second grasping member 512 to a sufficient extent to fully disengage stent 602 (e.g., by sufficiently radially contracting a medial portion of stent 602) from lumen wall 604, as shown in FIG. 8F. As is shown in FIGS. 8E, and 8F, distance 514 between first grasping member 510 and second grasping member 512 increases, resulting in reduction of the diameter of a medial portion of stent 602.

For example, in one or more embodiments, after the apparatus is in the first and second grasping configurations (e.g., each of first grasping member 510 and second grasping member 512 are grasping and radially contracting a respective portion of a collapsible medical device), pull mechanism 520 can be pulled to slide second grasping member 512 proximally toward stopper 518 and away from first grasping member 510. This mechanism is employed to increase distance 514 between first grasping member 510 and second grasping member 512, thereby disengaging stent 602 (e.g., medial portion 605 of stent 602) from lumen wall 604.

In one or more embodiments, disengaging a medial portion of a collapsible medical device from a lumen wall may be accomplished by distal movement of the first grasping member, proximal movement of the second grasping member, or combinations of both without limitation. For example, one may cycle between distal movement of the first grasping member and proximal movement of the second grasping member (e.g., any number of cycles) until the medial portion of the collapsible medical device disengages from the lumen wall. In one or more embodiments, the distal movement of the first grasping member and proximal movement of the second grasping member may occur simultaneously.

A description of some exemplary embodiments of the present disclosure is contained in one or more of the following numbered statements:

Statement 1. An apparatus for manipulating a collapsible medical device, the apparatus comprising:

a sheath having a distal end, the sheath defining a sheath lumen that terminates at a sheath distal opening and that extends axially through at least a portion of the sheath;

a first shaft comprising a first grasping member, the first shaft structured and arranged to slide axially within and relative to the sheath lumen from a delivery configuration to a grasping configuration;

a second grasping member structured and arranged to slide axially relative to the first shaft, the second grasping member separated from the first grasping member by a distance;

a balloon expandable from an engaged configuration to an elongated configuration, the balloon structured and arranged such that expansion of the balloon changes the distance.

Statement 2. The apparatus of statement 1 wherein the grasping configuration is a first grasping configuration and wherein the first shaft is structured and arranged to slide axially within and relative to the sheath lumen from the first grasping configuration to a second grasping configuration.

Statement 3. The apparatus of statement 1 or statement 2 wherein the expansion of the balloon comprises inflating the balloon with an inflation medium.

Statement 4. The apparatus of any of statements 1-3 wherein the first grasping member comprises a hinge.

Statement 5. The apparatus of any of statements 1-4 wherein the first grasping member comprises two jaws.

Statement 6. The apparatus of any of statements 1-5 wherein the second grasping member comprises a hinge.

Statement 7. The apparatus of any of statements 1-6 wherein a distal portion of the balloon engages the first grasping member, a proximal portion of the balloon engages the second grasping member, and expansion of the balloon causes an increase in the distance separating the first grasping member and the second grasping member.

Statement 8. The apparatus of any of statements 1-7 wherein the balloon engages the first grasping member, wherein the balloon is expandable to a first partially expanded configuration in which a first portion of the balloon has a first length, has a first diameter, and is disposed between the first grasping member and the second grasping member, and further in which a second portion of the balloon has a second length, a second diameter, and is disposed proximal of the second grasping member, and wherein the first diameter is greater than the second diameter.

Statement 9. The apparatus of statement 8 wherein the balloon is expandable to a second partially expanded configuration wherein the second length is shorter than the second length in the first partially expanded configuration.

Statement 10. An apparatus for manipulating a collapsible medical device, the apparatus comprising:
a sheath having a distal end, the sheath defining a sheath lumen that terminates at a sheath distal opening and that extends axially through at least a portion of the sheath;
a first shaft comprising a first grasping member, the first shaft structured and arranged to slide axially relative to the sheath within the sheath lumen from a delivery configuration, wherein the first grasping member is disposed at least partially within the sheath lumen, to a grasping configuration wherein the first grasping member is disposed distal of the sheath distal opening;
a second grasping member comprising a tubular member, the tubular member disposed about the sheath and structured and arranged to slide axially relative to the sheath.

Statement 11. The apparatus of statement 10 wherein the sheath defining a sheath lumen comprises an endoscope defining a working channel.

Statement 12. The apparatus of statement 10 or statement 11 wherein the tubular member is an endoscope cap.

Statement 13. The apparatus of any of statements 10-12 wherein, in the grasping configuration, the first grasping member is disposed at least partially within the sheath lumen.

Statement 14. The apparatus of any of statements 10-13 further comprising a stopper disposed proximal of the tubular member, the stopper being structured and arranged to obstruct sliding of the tubular member in the proximal direction.

Statement 15. A method of manipulating a collapsible medical device, the method comprising:
disposing an apparatus to the vicinity of a collapsible medical device, the apparatus comprising:
  a sheath having a sheath lumen,
  a first grasping member having a delivery configuration when disposed within the sheath lumen and a grasping configuration when disposed distal of the sheath lumen, and
  a second grasping member;
wherein the collapsible medical device longitudinally extends in an axial direction;
grasping a distal portion of the collapsible medical device with the first grasping member;
actuating the first grasping member to at least partially collapse the distal portion of the collapsible medical device;
grasping a proximal portion of the collapsible medical device with the second grasping member;
actuating the second grasping member to at least partially collapse the proximal portion of the collapsible medical device;
increasing the distance in the axial direction between the first grasping member and the second grasping member.

Statement 16. The method of statement 15 wherein increasing the distance between the first grasping member and the second grasping member comprises expanding at least a portion of a balloon disposed between the first grasping member and the second grasping member.

Statement 17. The method of statement 15 or statement 16 wherein increasing the distance in the axial direction A between the first grasping member and the second grasping member comprises axially translating one of the first grasping member and the second grasping member.

Statement 18. The method of any of statements 15-17 wherein increasing the distance in the axial direction A between the first grasping member and the second grasping member comprises simultaneously translating the sheath and the first grasping member in a distal direction relative to the second grasping member.

Statement 19. The method of any of statements 15-18 wherein the grasping of the distal portion of the collapsible device with the first grasping member occurs while at least a portion of the sheath is disposed within at least one of the distal portion, the medial portion, and the proximal portion portions of the collapsible medical device.

Statement 20. The method of any of statements 15-19 wherein increasing the distance in the axial direction between the first grasping member and the second grasping member comprises at least partially collapsing at least a medial portion of the collapsible medical device disposed between the distal portion and the proximal portion.

It should be understood that this disclosure is, in many respects, only illustrative. Changes may be made in details (e.g., matters of shape, size, and arrangement of components and/or steps) without exceeding the scope of the present disclosure. This may include, to the extent that it is appropriate, the use of any of the features of one embodiment being used in one or more other embodiments.

What is claimed is:

1. An apparatus for manipulating a collapsible medical device, the apparatus comprising:
   a sheath having a distal end, the sheath defining a sheath lumen that terminates at a sheath distal opening and that extends axially through at least a portion of the sheath;
   a first shaft comprising a first grasping member, the first shaft structured and arranged to slide axially within and relative to the sheath lumen from a delivery configuration to a grasping configuration;
   a second grasping member structured and arranged to slide axially relative to the first shaft, the second grasping member separated from the first grasping member by a distance;
   a balloon expandable from a deflated configuration to an elongated configuration, the balloon structured and arranged such that expansion of the balloon increases the distance.

2. The apparatus of claim 1 wherein the grasping configuration is a first grasping configuration and wherein the first shaft is structured and arranged to slide axially within and relative to the sheath lumen from the first grasping configuration to a second grasping configuration.

3. The apparatus of claim 1 wherein the expansion of the balloon comprises inflating the balloon with an inflation medium.

4. The apparatus of claim 1 wherein the first grasping member comprises a hinge.

5. The apparatus of claim 1 wherein the first grasping member comprises two jaws.

6. The apparatus of claim 1 wherein the second grasping member comprises a hinge.

7. The apparatus of claim 1 wherein the balloon engages the first grasping member, wherein the balloon is expandable to a first partially expanded configuration in which a first portion of the balloon has a first length, has a first diameter, and is disposed between the first grasping member and the second grasping member, and further in which a second portion of the balloon has a second length, a second diameter, and is disposed proximal of the second grasping member, and wherein the first diameter is greater than the second diameter.

8. The apparatus of claim 7 wherein the balloon is expandable to a second partially expanded configuration wherein the second length is shorter than the second length in the first partially expanded configuration.

9. An apparatus for manipulating a collapsible medical device, the apparatus comprising:
- a sheath having a distal end, the sheath defining a sheath lumen that terminates at a sheath distal opening and that extends axially through at least a portion of the sheath;
- a first shaft comprising a first grasping member, the first shaft structured and arranged to slide axially within and relative to the sheath lumen from a delivery configuration to a grasping configuration;
- a second grasping member structured and arranged to slide axially relative to the first shaft, the second grasping member separated from the first grasping member by a distance;
- a balloon expandable from a deflated configuration to an elongated configuration, the balloon structured and arranged such that expansion of the balloon changes the distance; and
- wherein a distal portion of the balloon engages the first grasping member, a proximal portion of the balloon engages the second grasping member, and expansion of the balloon causes an increase in the distance separating the first grasping member and the second grasping member.

10. An apparatus for manipulating a collapsible medical device, the apparatus comprising:
- a first elongate shaft;
- a first grasping member disposed on a distal end region of the first elongate shaft, the first grasping member being actuatable from a delivery configuration to a grasping configuration;
- a second grasping member disposed proximal of the first grasping member and configured to slide axially relative to the first elongate shaft, the second grasping member being actuatable from a delivery configuration to a grasping configuration, the second grasping member separated from the first grasping member by a distance;
- a balloon arranged between the first grasping member and the second grasping member, wherein expansion of the balloon increases the distance between the first grasping member and the second grasping member.

11. The apparatus of claim 10, wherein the first grasping member comprises at least two jaws.

12. The apparatus of claim 11, further comprising one or more pull wires extending along the first elongate shaft, wherein the one or more pull wires are configured to actuate the at least two jaws.

13. The apparatus of claim 10, wherein the second grasping member is attached to a distal end of a second elongate shaft.

14. The apparatus of claim 13, wherein the second elongate shaft is slidably disposed around the first elongate shaft.

15. The apparatus of claim 13, wherein the second grasping member comprises at least two jaws.

16. The apparatus of claim 15, further comprising one or more pull wires extending along the second elongate shaft, wherein the one or more pull wires are configured to actuate the at least two jaws.

\* \* \* \* \*